(12) United States Patent
Eldred

(10) Patent No.: US 8,173,067 B2
(45) Date of Patent: May 8, 2012

(54) ORGANIC COMPOUND AND METAL ION SYNERGISTIC DISINFECTION AND PURIFICATION SYSTEM AND METHOD OF MANUFACTURE

(75) Inventor: Bradley J. Eldred, Underhill, VT (US)

(73) Assignee: Bradley J. Eldred, Underhill, VT (US)

( * ) Notice: Subject to any disclaimer, the term of this patent is extended or adjusted under 35 U.S.C. 154(b) by 0 days.

(21) Appl. No.: 12/984,983

(22) Filed: Jan. 5, 2011

(65) Prior Publication Data
US 2011/0165263 A1   Jul. 7, 2011

Related U.S. Application Data

(63) Continuation of application No. 11/947,314, filed on Nov. 29, 2007, now Pat. No. 7,887,749, which is a continuation of application No. 10/679,660, filed on Oct. 6, 2003, now Pat. No. 7,485,259.

(60) Provisional application No. 60/416,817, filed on Oct. 8, 2002.

(51) Int. Cl.
| | |
|---|---|
| B01J 19/00 | (2006.01) |
| A61L 2/00 | (2006.01) |
| A61L 9/01 | (2006.01) |
| A61K 7/06 | (2006.01) |
| A01N 25/34 | (2006.01) |
| A01N 55/02 | (2006.01) |
| C02F 5/02 | (2006.01) |
| C02F 1/68 | (2006.01) |
| E04H 3/16 | (2006.01) |

(52) U.S. Cl. ............... 422/28; 422/1; 422/41; 422/261; 422/292; 422/900; 422/901; 424/408; 424/76.8; 424/618; 424/630; 424/736; 424/76.1; 424/725; 424/58; 424/74; 424/76.9; 210/764; 210/758; 210/749; 210/167; 210/169; 514/495; 514/499; 514/783; 252/175

(58) Field of Classification Search ............... 422/1, 28, 422/41, 261, 292, 900–901; 424/408, 76.8, 424/618, 630, 736, 76.1, 725, 58, 74, 76.9; 210/764, 758, 749, 167, 169; 514/495, 499, 514/783; 252/175

See application file for complete search history.

(56) References Cited

U.S. PATENT DOCUMENTS 4,098,602 A   7/1978   Seymour et al.
(Continued)

FOREIGN PATENT DOCUMENTS

DE   1642001   4/1971
(Continued)

OTHER PUBLICATIONS

Bulletin of the Korean Fisheries Society, "Studies on the antimicrobial activity of grapefruit seed extract", Choi JD, vol. 23, No. 4, pp. 297-302, 1990.*

(Continued)

*Primary Examiner* — Jill Warden
*Assistant Examiner* — Monzer Chorbaji
(74) *Attorney, Agent, or Firm* — Morgan, Lewis & Bockius LLP

(57) ABSTRACT

A new, novel and useful disinfection and purification system comprised of organic compounds in synergistic action with selected metal ions and method of manufacture and use. One of the benefits that is derived from this system is the ability to quickly and easily treat a surface, fluid or medium for disinfection of bacteria, fungi, viruses, algae and protozoans, with a non-toxic, non-chlorinated mixture that effectively kills all such organisms in minutes or hours. The disinfection and purification system remains effective for long periods of time maintaining its disinfection capacity making it highly effective for stored or transported mediums such as potable drinking water. The disinfection and purification system may be incorporated with carbon block or membrane filters to disinfect filtered liquids such as water to render it potable. The disinfection and purification system may be infused into semi-permeable surfaces or applied to non-porous surfaces such that the disinfectant compounds of the system would be delivered to surface of an object to be disinfected by leaching, capillary action, mere contact, water activation and/or osmosis/diffusion.

6 Claims, 16 Drawing Sheets

Filename: Residual Study Summary Version1.xls
Filedate: August 8, 2003

Results in Scientific Notation:
No results excluded

Klebsiella terrigena
Run Results - CFUs/mL by contact time (min)

| Run Date | MPT "age" (weeks) | MPT Run # | Sample # | Challenge Dose | T30 | T60 | T90 |
|---|---|---|---|---|---|---|---|
| 31-Mar-03 | 0 | 10 | 2 | 5.0 x 10^6 | | 0 | |
| | | | 3 | | | 0 | |
| 15-Apr-03 | 2 | 13 | 4 | 4.9 x 10^6 | 2.5 x 10^2 | 0 | 0 |
| | | | 5 | | 1.4 x 10^2 | 0 | 0 |
| 30-Apr-03 | 4 | 15 | 4 | 8.7 x 10^6 | 2.4 x 10^3 | 0 | 0 |
| | | | 5 | | 2.3 x 10^3 | 0 | 0 |
| 2-May-03 | 4 | 16 | 4 | 5.0 x 10^6 | 9.9 x 10^1 | 0 | 0 |
| | | | 5 | | 5.3 x 10^3 | 0 | 0 |
| 6-May-03 | 5 | 17 | 4 | 4.8 x 10^6 | 4 | 0 | 0 |
| | | | 5 | | 2.1 x 10^2 | 5.4 x 10^1 | 0 |
| 20-May-03 | 7 | 20 | 4 | 6.9 x 10^6 | 1 | 0 | 0 |
| | | | 5 | | 8.4 x 10^1 | 0 | 0 |
| 29-May-03 | 7 | 21 | 4 | 4.5x 10^6 | 1.4 x 10^2 | 0 | 0 |
| | | | 5 | | 2.3 x 10^2 | 0 | 0 |
| 17-Jun-03 | 11 | 22 | 4 | 1.1 x 10^7 | 8.5 x 10^2 | 0 | 0 |
| | | | 5 | | 2.7 x 10^3 | 0 | 0 |
| 15-Jul-03 | 15 | 24 | 4 | 1.0 x 10^7 | 8.6 x 10^2 | 0 | 0 |
| | | | 5 | | 4.4 x 10^3 | 0 | 0 |
| 7-Aug-03 | 18 | 29 | 6 | 1.2 x 10^7 | 8.7 x 10^2 | 2.0 x 10^1 | 0 |
| | | | 7 | | 2.4 x 10^7 | 3.0 x 10^3 | 1 | 0 |
| 25-Aug-03 | 21 | 32 | 5 | 8.0 x 10^6 | 6.1 x 10^4 | 8 | 0 |
| | | | 6 | | 2.9 x 10^4 | 0 | 0 |

Note: 7 Aug 03 sample #7 was challenged at 2X dose of #6 sample

Results in Number Format
No results excluded

Klebsiella terrigena
Run Results - CFUs/mL by contact time (min)

| Run Date | MPT "age" (weeks) | MPT Run # | Sample # | Challenge Dose | T30 | T60 | T90 |
|---|---|---|---|---|---|---|---|
| 15-Apr-03 | 2 | 13 | 4 | 4,900,000 | 250 | 0 | 0 |
| | | | 5 | | 140 | 0 | 0 |
| 30-Apr-03 | 4 | 15 | 4 | 8,700,000 | 2,400 | 0 | 0 |
| | | | 5 | | 2,300 | 0 | 0 |
| 2-May-03 | 4 | 16 | 4 | 5,000,000 | 99 | 0 | 0 |
| | | | 5 | | 5,300 | 0 | 0 |
| 6-May-03 | 5 | 17 | 4 | 4,800,000 | 4 | 0 | 0 |
| | | | 5 | | 210 | 54 | 0 |
| 20-May-03 | 7 | 20 | 4 | 6,900,000 | 1 | 0 | 0 |
| | | | 5 | | 84 | 0 | 0 |
| 29-May-03 | 7 | 21 | 4 | 4,500,000 | 140 | 0 | 0 |
| | | | 5 | | 230 | 0 | 0 |
| 17-Jun-03 | 11 | 22 | 4 | 11,000,000 | 850 | 0 | 0 |
| | | | 5 | | 2,700 | 0 | 0 |
| 15-Jul-03 | 15 | 24 | 4 | 10,000,000 | 860 | 0 | 0 |
| | | | 5 | | 4,400 | 1 | 0 |
| 7-Aug-03 | 18 | 29 | 6 | 12,000,000 | 870 | 20 | 0 |
| | | | 7 | | 24,000,000 | 3,000 | 1 | 0 |
| 25-Aug-03 | 21 | 32 | 5 | 8,000,000 | 61,000 | 8 | 0 |
| | | | 6 | | 29,000 | 0 | 0 |

Note: 7 Aug 03 sample #7 was challenged at 2X dose of #6 sample

U.S. PATENT DOCUMENTS

| | | | |
|---|---|---|---|
| 4,229,410 | A | 10/1980 | Kosti |
| 4,490,389 | A | 12/1984 | Nelson et al. |
| 4,909,986 | A | 3/1990 | Kobayashi et al. |
| 4,952,398 | A | 8/1990 | Tapin |
| 5,217,626 | A | 6/1993 | Yahya et al. |
| 5,387,394 | A | 2/1995 | Baker |
| 5,425,944 | A | 6/1995 | Harich |
| 5,510,109 | A | 4/1996 | Tomioka et al. |
| 5,997,814 | A | 12/1999 | Minerovic et al. |
| 6,132,750 | A | 10/2000 | Perrier et al. |
| 6,197,814 | B1 | 3/2001 | Arata |
| 6,379,720 | B1 | 4/2002 | Cooper et al. |
| 6,500,406 | B1 | 12/2002 | Rajaiah et al. |
| 6,541,606 | B2 | 4/2003 | Margolin et al. |
| 6,596,401 | B1 | 7/2003 | Terry et al. |
| 6,899,903 | B2 | 5/2005 | Quillin |
| 7,087,249 | B2 * | 8/2006 | Burrell et al. ............... 424/618 |
| 7,455,851 | B1 * | 11/2008 | Nelson et al. ............... 424/406 |
| 7,485,259 | B2 | 2/2009 | Eldred |
| 7,887,749 | B2 | 2/2011 | Eldred |

FOREIGN PATENT DOCUMENTS

| | | |
|---|---|---|
| DE | 19917836 | 10/2000 |
| JP | 405253581 | 10/1993 |
| JP | 07062397 | 3/1995 |
| JP | 10000477 | 1/1998 |
| JP | 2000026221 | 1/2000 |
| RU | 2179155 | 2/2002 |
| WO | 9316597 | 9/1993 |
| WO | 9522254 | 8/1995 |
| WO | 9918790 | 4/1999 |
| WO | 9937584 | 7/1999 |
| WO | 9949731 | 10/1999 |
| WO | 02069708 | 9/2002 |
| WO | 02083599 | 10/2002 |

OTHER PUBLICATIONS

Swicegood, C.,"The Kitchen Physician, Grapefruit Seed Abstract, Cure and Disinfect," pp. 1-4, Dec. 7, 1998.

Taylor, R., "Standardized Grapefruit Extract", pp. 1-4, Oct. 2, 1999.

Choi, J.D., Bulletin of the Korean Fisheries Society, "Studies on the Antimicrobial Activity of Grapefruit Seed Extract", vol. 23, No. 4, pp. 297-302, 1990.

Domek, M. et al., "Evidence for the Role of Copper in the Injury Process of Coliform Bacteria in Drinking Water", Appl. Environ. Microbiol., 48: pp. 289-293, 1984.

Landeen et al., "Efficacy of Copper/Silver Ion & Reduced Levels of Free Chlorine . . . " Appl. Environ. Microbiol., 55: pp. 3045-3050, 1989.

Kutz et al., "Microbiological Evaluation of Copper: Silver Disinfection Units", Proc. of the Fourth Conference on Progress in Clinical Disinfection, S.U.N.Y., Apr. 11-13, 1988.

Yahya et al., "Disinfection of Bacteria in Water Systems by Using Electrolytically Generated Copper . . . ", CA J. Microbiol. 36: pp. 109-116.

Margolin et al., "Control of Microorganisms in Source Water and Drinking Water", Manual Envir. Microbiol., Washington D.C., pp. 274-284, 2002.

Derwent and West Translation of the abstract of JP07062397.

Abad et al., "Dininfection of Human Enteric Viruses re Water by Copper Silver . . . " Appl. Environ. Microbiol., 60(7): pp. 2377-2383, 1994.

Lin et al., "individual and Combined Effects of Copper and Silver Ions on Inactivation of . . . ", Wat. Res. 30(8): pp. 1905-1913, 1996.

Rohr et al., "Impact of Silver and Copper on the Survival of Amoebae and Ciliated Protoza in Vitro", Int. J. Hyg. Environ. Health 203: pp. 87-89, 2000.

Batterman et al., "Evaluation of the Efficacy of a New Secondary Disinfectant Formulation Using Hydrogen Peroxide . . . ", STAR Grant No. R825362, 2001.

International Preliminary Examination Report of PCT/US2003/031560 dated Sep. 28, 2004, 4 pages.

International Search Report of PCT/US2003/031560 dated Jun. 16, 2004, 2 pages.

Publication of PCT/US2003/031560 dated Apr. 22, 2004, 41 pages.

EP Supplementary Partial Search Report dated Mar. 22, 2006 for EP Application No. 03773167, 7 pages.

EP Supplementary Search Report dated Jun. 14, 2006 for EP Application No. 03773167, 8 pages.

Derwent and West Translation of the abstract of JP07062397, pp. 1-3, Sep. 30, 2005.

* cited by examiner

Figure 6A

Filename: Residual Study Summary Version1.xls
Filedate: August 8, 2003

Results in Scientific Notation:
No results excluded

| | | | | | Klebsiella terrigena | | |
| | | | | | Run Results - CFUs/mL by contact time (min) | | |
| Run Date | MPT "age" (weeks) | MPT Run # | Sample # | Challenge Dose | T30 | T60 | T90 |
|---|---|---|---|---|---|---|---|
| 31-Mar-03 | 0 | 10 | 2 | $5.0 \times 10^6$ | | 0 | |
| | | | 3 | | | 0 | |
| 15-Apr-03 | 2 | 13 | 4 | $4.9 \times 10^6$ | $2.5 \times 10^2$ | 0 | 0 |
| | | | 5 | | $1.4 \times 10^2$ | 0 | 0 |
| 30-Apr-03 | 4 | 15 | 4 | $8.7 \times 10^6$ | $2.4 \times 10^3$ | 0 | 0 |
| | | | 5 | | $2.3 \times 10^3$ | 0 | 0 |
| 2-May-03 | 4 | 16 | 4 | $5.0 \times 10^6$ | $9.9 \times 10^1$ | 0 | 0 |
| | | | 5 | | $5.3 \times 10^3$ | 0 | 0 |
| 6-May-03 | 5 | 17 | 4 | $4.8 \times 10^6$ | 4 | 0 | 0 |
| | | | 5 | | $2.1 \times 10^2$ | $5.4 \times 10^1$ | 0 |
| 20-May-03 | 7 | 20 | 4 | $6.9 \times 10^6$ | 1 | 0 | 0 |
| | | | 5 | | $8.4 \times 10^1$ | 0 | 0 |
| 29-May-03 | 7 | 21 | 4 | $4.5 \times 10^6$ | $1.4 \times 10^2$ | 0 | 0 |
| | | | 5 | | $2.3 \times 10^2$ | 0 | 0 |
| 17-Jun-03 | 11 | 22 | 4 | $1.1 \times 10^7$ | $8.5 \times 10^2$ | 0 | 0 |
| | | | 5 | | $2.7 \times 10^3$ | 0 | 0 |
| 15-Jul-03 | 15 | 24 | 4 | $1.0 \times 10^7$ | $8.6 \times 10^2$ | 0 | 0 |
| | | | 5 | | $4.4 \times 10^3$ | 1 | 0 |
| 7-Aug-03 | 18 | 29 | 6 | $1.2 \times 10^7$ | $8.7 \times 10^2$ | $2.0 \times 10^1$ | 0 |
| | | | 7 | $2.4 \times 10^7$ | $3.0 \times 10^3$ | 1 | 0 |
| 25-Aug-03 | 21 | 32 | 5 | $8.0 \times 10^6$ | $6.1 \times 10^4$ | 8 | 0 |
| | | | 6 | | $2.9 \times 10^4$ | 0 | 0 |

Note: 7 Aug 03 sample #7 was challenged at 2X dose of #6 sample

Figure 6A (continued)

Results in Number Format
No results excluded

| | | | | Klebsiella terrigena | | | |
|---|---|---|---|---|---|---|---|
| | | | | Run Results - CFUs/mL by contact time (min) | | | |
| Run Date | MPT "age" (weeks) | MPT Run # | Sample # | Challenge Dose | T30 | T60 | T90 |
| 15-Apr-03 | 2 | 13 | 4 | 4,900,000 | 250 | 0 | 0 |
| | | | 5 | | 140 | 0 | 0 |
| 30-Apr-03 | 4 | 15 | 4 | 8,700,000 | 2,400 | 0 | 0 |
| | | | 5 | | 2,300 | 0 | 0 |
| 2-May-03 | 4 | 16 | 4 | 5,000,000 | 99 | 0 | 0 |
| | | | 5 | | 5,300 | 0 | 0 |
| 6-May-03 | 5 | 17 | 4 | 4,800,000 | 4 | 0 | 0 |
| | | | 5 | | 210 | 54 | 0 |
| 20-May-03 | 7 | 20 | 4 | 6,900,000 | 1 | 0 | 0 |
| | | | 5 | | 84 | 0 | 0 |
| 29-May-03 | 7 | 21 | 4 | 4,500,000 | 140 | 0 | 0 |
| | | | 5 | | 230 | 0 | 0 |
| 17-Jun-03 | 11 | 22 | 4 | 11,000,000 | 850 | 0 | 0 |
| | | | 5 | | 2,700 | 0 | 0 |
| 15-Jul-03 | 15 | 24 | 4 | 10,000,000 | 860 | 0 | 0 |
| | | | 5 | | 4,400 | 1 | 0 |
| 7-Aug-03 | 18 | 29 | 6 | 12,000,000 | 870 | 20 | 0 |
| | | | 7 | 24,000,000 | 3,000 | 1 | 0 |
| 25-Aug-03 | 21 | 32 | 5 | 8,000,000 | 61,000 | 8 | 0 |
| | | | 6 | | 29,000 | 0 | 0 |

Note: 7 Aug 03 sample #7 was challenged at 2X dose of #6 sample

Figure 6A (continued)

Results in Log Format
No results excluded

| Run Date | MPT "age" (weeks) | MPT Run # | Sample # | Klebsiella terrigena Challenge Dose | Run Results - CFUs/mL by contact time (min) T30 | T60 | T90 |
|---|---|---|---|---|---|---|---|
| 31-Mar-03 | 0 | 10 | 2 | 6.70 | | 0.0 | |
| | | | 3 | 6.70 | | 0.0 | |
| 15-Apr-03 | 2 | 13 | 4 | 6.69 | 2.40 | 0.0 | 0.0 |
| | | | 5 | 6.69 | 2.15 | 0.0 | 0.0 |
| 30-Apr-03 | 4 | 15 | 4 | 6.94 | 3.38 | 0.0 | 0.0 |
| | | | 5 | 6.94 | 3.36 | 0.0 | 0.0 |
| 2-May-03 | 4 | 16 | 4 | 6.70 | 2.00 | 0.0 | 0.0 |
| | | | 5 | 6.70 | 3.72 | 0.0 | 0.0 |
| 6-May-03 | 5 | 17 | 4 | 6.68 | 0.60 | 0.0 | 0.0 |
| | | | 5 | 6.68 | 2.32 | 1.73 | 0.0 |
| 20-May-03 | 7 | 20 | 4 | 6.84 | 0.00 | 0.0 | 0.0 |
| | | | 5 | 6.84 | 1.92 | 0.0 | 0.0 |
| 29-May-03 | 7 | 21 | 4 | 6.65 | 2.15 | 0.0 | 0.0 |
| | | | 5 | 6.65 | 2.36 | 0.0 | 0.0 |
| 17-Jun-03 | 11 | 22 | 4 | 7.04 | 2.93 | 0.0 | 0.0 |
| | | | 5 | 7.04 | 3.43 | 0.0 | 0.0 |
| 15-Jul-03 | 15 | 24 | 4 | 7.00 | 2.93 | 0.0 | 0.0 |
| | | | 5 | 7.00 | 3.64 | 0.00 | 0.0 |
| 7-Aug-03 | 18 | 29 | 6 | 7.08 | 2.94 | 1.30 | 0.0 |
| | | | 7 | 7.38 | 3.48 | 0.00 | 0.0 |
| 25-Aug-03 | 21 | 32 | 5 | 6.90 | 4.79 | 0.90 | 0.0 |
| | | | 6 | 6.90 | 4.46 | 0.0 | 0.0 |

Note: 7 Aug 03 sample #7 was challenged at 2X dose of #6 sample
Note: For log value, a "1" is reported as 0.00 and a "0" is reported as 0.0 and will be indicated as ">" in log reductions Makeup Water: CWD finished water, carbon filter, 1 micron nominal filtration, UV.
Water Chemistry: - 3/31/03 (pre MPT addition)
        pH - 7.15        TDS - 132.5
        Turb - 0.19      Conductivity - 199.8 micromhos/cm
        Temp - 22.0    Total Chlorine - <0.03 mg/L
        5/29/03 (MPT in water)
        pH - 7.84        TDS - 144.6 mg/L
        Turb - 0.57 NTU  Conductivity - 217 micromhos/cm
        Temp - 21.5 ' C   Total Chlorine - <0.03 mg/L

Figure 6B

Log Reductions
No Results Excluded

| Run Date | MPT "age" (weeks) | MPT Run # | Sample # | Klebsiella terrigena Run Results - CFUs/mL by contact time (min) | | | |
|---|---|---|---|---|---|---|---|
| | | | | Challenge Dose | T30 | T60 | T90 |
| 31-Mar-03 | 0 | 10 | 2 | 6.70 | | 6.70 | |
| | | | 3 | 6.70 | | 6.70 | |
| 15-Apr-03 | 2 | 13 | 4 | 6.69 | 4.29 | 6.69 | 6.69 |
| | | | 5 | 6.69 | 4.54 | 6.69 | 6.69 |
| 30-Apr-03 | 4 | 15 | 4 | 6.94 | 3.56 | 6.94 | 6.94 |
| | | | 5 | 6.94 | 3.58 | 6.94 | 6.94 |
| 2-May-03 | 4 | 16 | 4 | 6.70 | 4.70 | 6.70 | 6.70 |
| | | | 5 | 6.70 | 2.98 | 6.70 | 6.70 |
| 6-May-03 | 5 | 17 | 4 | 6.68 | 6.08 | 6.68 | 6.68 |
| | | | 5 | 6.68 | 4.36 | 4.95 | 6.68 |
| 20-May-03 | 7 | 20 | 4 | 6.84 | 6.84 | 6.84 | 6.84 |
| | | | 5 | 6.84 | 4.92 | 6.84 | 6.84 |
| 29-May-03 | 7 | 21 | 4 | 6.65 | 4.50 | 6.65 | 6.65 |
| | | | 5 | 6.65 | 4.29 | 6.65 | 6.65 |
| 17-Jun-03 | 11 | 22 | 4 | 7.04 | 4.11 | 7.04 | 7.04 |
| | | | 5 | 7.04 | 3.61 | 7.04 | 7.04 |
| 15-Jul-03 | 15 | 24 | 4 | 7.00 | 4.07 | 7.00 | 7.00 |
| | | | 5 | 7.00 | 3.36 | 7.00 | 7.00 |
| 7-Aug-03 | 18 | 29 | 6 | 7.08 | 4.14 | 5.78 | 7.08 |
| | | | 7 | 7.38 | 3.90 | 7.38 | 7.38 |
| 25-Aug-03 | 21 | 32 | 5 | 6.90 | 2.11 | 6.00 | 6.90 |
| | | | 6 | 6.90 | 2.44 | 6.90 | 6.90 |

Note: 7 Aug 03 sample #7 was challenged at 2X dose of #6 sample

Figure 6B (continued)

Results in Log Format
May 6 and Aug 7 "flyer" results at 60 minutes excluded    Klebsiella terrigena

| | | | | | Run Results - CFUs/mL by contact time (min) | | |
|---|---|---|---|---|---|---|---|
| Run Date | MPT "age" (weeks) | MPT Run # | Sample # | Challenge Dose | T30 | T60 | T90 |
| 31-Mar-03 | 0 | 10 | 2 | 6.70 | | 0.0 | |
| | | | 3 | 6.70 | | 0.0 | |
| 15-Apr-03 | 2 | 13 | 4 | 6.69 | 2.40 | 0.0 | 0.0 |
| | | | 5 | 6.69 | 2.15 | 0.0 | 0.0 |
| 30-Apr-03 | 4 | 15 | 4 | 6.94 | 3.38 | 0.0 | 0.0 |
| | | | 5 | 6.94 | 3.36 | 0.0 | 0.0 |
| 2-May-03 | 4 | 16 | 4 | 6.70 | 2.00 | 0.0 | 0.0 |
| | | | 5 | 6.70 | 3.72 | 0.0 | 0.0 |
| 6-May-03 | 5 | 17 | 4 | 6.68 | 0.60 | 0.0 | 0.0 |
| | | | 5 | 6.68 | 2.32 | | 0.0 |
| 20-May-03 | 7 | 20 | 4 | 6.84 | 0.00 | 0.0 | 0.0 |
| | | | 5 | 6.84 | 1.92 | 0.0 | 0.0 |
| 29-May-03 | 7 | 21 | 4 | 6.65 | 2.15 | 0.0 | 0.0 |
| | | | 5 | 6.65 | 2.36 | 0.0 | 0.0 |
| 17-Jun-03 | 11 | 22 | 4 | 7.04 | 2.93 | 0.0 | 0.0 |
| | | | 5 | 7.04 | 3.43 | 0.0 | 0.0 |
| 15-Jul-03 | 15 | 24 | 4 | 7.00 | 2.93 | 0.0 | 0.0 |
| | | | 5 | 7.00 | 3.64 | 0.00 | 0.0 |
| 7-Aug-03 | 18 | 29 | 6 | 7.08 | 2.94 | | 0.0 |
| | | | 7 | 7.38 | 3.48 | 0.00 | 0.0 |
| 25-Aug-03 | 21 | 32 | 5 | 6.90 | 4.79 | 0.90 | 0.00 |
| | | | 6 | 6.90 | 4.46 | 0.00 | 0.00 |

Note: 7 Aug 03 sample #7 was challenged at 2X dose of #6 sample

Figure 6C

Log Reductions
May 6 and Aug 7 "flyer" results at 60 minutes excluded

Klebsiella terrigena

| Run Date | MPT "age" (weeks) | MPT Run # | Sample # | Challenge Dose | T30 | T60 | T90 |
|---|---|---|---|---|---|---|---|
| 31-Mar-03 | 0 | 10 | 2 | 6.70 | | 6.70 | |
| | | | 3 | 6.70 | | 6.70 | |
| 15-Apr-03 | 2 | 13 | 4 | 6.69 | 4.29 | 6.69 | 6.69 |
| | | | 5 | 6.69 | 4.54 | 6.69 | 6.69 |
| 30-Apr-03 | 4 | 15 | 4 | 6.94 | 3.56 | 6.94 | 6.94 |
| | | | 5 | 6.94 | 3.58 | 6.94 | 6.94 |
| 2-May-03 | 4 | 16 | 4 | 6.70 | 4.70 | 6.70 | 6.70 |
| | | | 5 | 6.70 | 2.98 | 6.70 | 6.70 |
| 6-May-03 | 5 | 17 | 4 | 6.68 | 6.08 | 6.68 | 6.68 |
| | | | 5 | 6.68 | 4.36 | | 6.68 |
| 20-May-03 | 7 | 20 | 4 | 6.84 | 6.84 | 6.84 | 6.84 |
| | | | 5 | 6.84 | 4.92 | 6.84 | 6.84 |
| 29-May-03 | 7 | 21 | 4 | 6.65 | 4.50 | 6.65 | 6.65 |
| | | | 5 | 6.65 | 4.29 | 6.65 | 6.65 |
| 17-Jun-03 | 11 | 22 | 4 | 7.04 | 4.11 | 7.04 | 7.04 |
| | | | 5 | 7.04 | 3.61 | 7.04 | 7.04 |
| 15-Jul-03 | 15 | 24 | 4 | 7.00 | 4.07 | 7.00 | 7.00 |
| | | | 5 | 7.00 | 3.36 | 7.00 | 7.00 |
| 7-Aug-03 | 18 | 29 | 6 | 7.08 | 4.14 | | 7.08 |
| | | | 7 | 7.38 | 3.90 | 7.38 | 7.38 |
| 25-Aug-03 | 21 | 32 | 5 | 6.90 | 2.11 | 6.00 | 6.90 |
| | | | 6 | 6.90 | 2.44 | 6.90 | 6.90 |

Note: 7 Aug 03 sample #7 was challenged at 2X dose of #6 sample

Figure 6C (continued)

Graph Values - May 6 and August 7 "flyer" results at 60 minutes excluded

|           | 30 min | 60 min | 90 min | 120 min | challenge level |   |
|-----------|--------|--------|--------|---------|-----------------|---|
| 31-Mar-03 |        | 6.7    |        |         | 6.7             |   |
|           |        | 6.7    |        |         | 6.7             |   |
| 15-Apr-03 | 4.29   | 6.69   | 6.69   |         | 6.69            |   |
|           | 4.54   | 6.69   | 6.69   |         | 6.69            |   |
| 30-Apr-03 | 3.56   | 6.94   | 6.94   |         | 6.94            |   |
|           | 3.58   | 6.94   | 6.94   |         | 6.94            |   |
| 2-May-03  | 4.7    | 6.7    | 6.7    |         | 6.7             |   |
|           | 2.98   | 6.7    | 6.7    |         | 6.7             |   |
| 6-May-03  | 6.08   | 6.68   | 6.68   |         | 6.68            |   |
|           | 4.36   |        | 6.68   |         | 6.68            |   |
| 20-May-03 | 6.84   | 6.84   | 6.84   |         | 6.84            |   |
|           | 4.92   | 6.84   | 6.84   |         | 6.84            |   |
| 29-May-03 | 4.5    | 6.65   | 6.65   |         | 6.65            |   |
|           | 4.29   | 6.65   | 6.65   |         | 6.65            |   |
| 17-Jun-03 | 4.11   | 7.04   | 7.04   |         | 7.04            |   |
|           | 3.61   | 7.04   | 7.04   |         | 7.04            |   |
| 15-Jul-03 | 4.07   | 7      | 7      |         | 7               |   |
|           | 3.36   | 7      | 7      |         | 7               |   |
| 7-Aug-03  | 4.14   |        | 7.08   |         | 7.08            |   |
|           | 3.6    | 7.38   | 7.38   |         | 7.38            |   |
| 25-Aug-03 | 2.11   | 6      | 6.9    |         | 6.9             |   |
|           | 2.44   | 6.9    | 6.9    |         | 6.9             |   |

Average values - 1 per date: for graphing Chart 1

| 31-Mar-03 |       | 6.7  |      | 6.7  | 0  |
|-----------|-------|------|------|------|----|
| 15-Apr-03 | 4.415 | 6.69 | 6.69 | 6.69 | 2  |
| 30-Apr-03 | 3.57  | 6.94 | 6.94 | 6.94 | 4  |
| 2-May-03  | 3.84  | 6.7  | 6.7  | 6.7  | 4  |
| 6-May-03  | 5.22  | 6.68 | 6.68 | 6.68 | 5  |
| 20-May-03 | 5.88  | 6.84 | 6.84 | 6.84 | 7  |
| 29-May-03 | 4.395 | 6.65 | 6.65 | 6.65 | 7  |
| 17-Jun-03 | 3.86  | 7.04 | 7.04 | 7.04 | 11 |
| 15-Jul-03 | 3.715 | 7    | 7    | 7    | 15 |
| 7-Aug-03  | 3.87  | 7.38 | 7.38 | 7.38 | 18 |
| 25-Aug-03 | 2.275 | 6.4  | 6.9  | 6.9  | 21 |

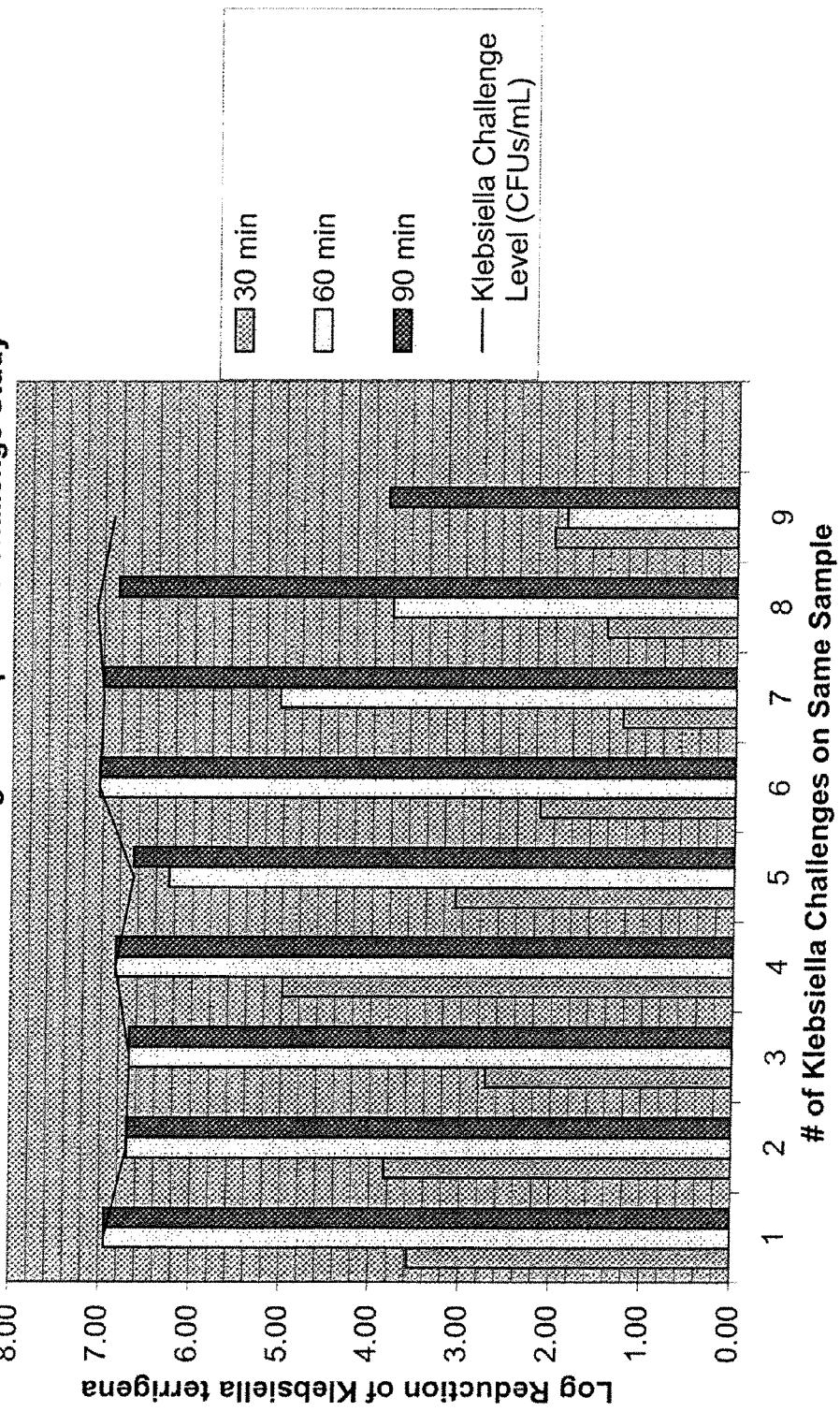

Figure 8A

Filename: Repetitive Challenge Summary Version1.xls
Filedate: 11 August 2003

Results in Scientific Notation
No results excluded

| | | | | Klebsiella terrigena ||||| 
| | | | | Run Results - CFUs/mL by contact time (min) ||||| 
| Run Date | # Of Inoculations | MPT Run # | Sample # | Challenge Dose | T30 | T60 | T90 | T120 |
|---|---|---|---|---|---|---|---|---|
| 30-Apr-03 | 1 | 15 | 4 | 8.7 x 10^6 | 2.4 x 10^3 | 0 | 0 | |
| | | | 5 | | 2.3 x 10^3 | 0 | 0 | |
| 2-May-03 | 2 | 16 | 4 | 5.0 x 10^6 | 9.9 x 10^1 | 0 | 0 | |
| | | | 5 | | 5.3 x 10^3 | 0 | 0 | |
| 6-May-03 | 3 | 17 | 6 | 4.8 x 10^6 | 1.6 x 10^4 | 0 | 0 | |
| | | | 7 | | 5.2 x 10^3 | 0 | 0 | |
| 20-May-03 | 4 | 20 | 6 | 6.9 x 10^6 | 5.0 x 10^1 | 0 | 0 | |
| | | | 7 | | 1.0 x 10^2 | 1.8 x 10^1* | 0 | |
| 29-May-03 | 5 | 21 | 6 | 4.5 x 10^6 | 1.4 x 10^5 | 2 | 0 | |
| | | | 7 | | 1.0 x 10^2 | 3 | 0 | |
| 17-Jun-03 | 6 | 22 | 6 | 1.1 x 10^7 | 4.2 x 10^4 | 0 | 1 | |
| | | | 7 | | 1.4 x 10^5 | 1 | 0 | |
| 15-Jul-03 | 7 | 24 | 6 | 1.0 x 10^7 | 7.0 x 10^5 | 1.0 x 10^2 | 0 | |
| | | | 7 | | 4.6 x 10^5* | 8.2 X 10^1 | 0 | |
| 7-Aug-03 | 8 | 29 | 6 | 1.2 x 10^7 | 4.3 x 10^5 | 1.5 x 10^3 | 3 | |
| | | | 7 | | 4.8 x 10^5 | 2.4 x 10^3 | 1 | |
| 25-Aug-03 | 9 | 32 | 5 | 8.0 x 10^6 | 7.6 x 10^4 | 6.8 x 10^4 | 2.0 x 10^3 | 5.3 x 10^1 |
| | | | 6 | | - | 1.6 x 10^5 | 6.2 x 10^2 | 8 |

Figure 8A (continued)

Results in Number Format
No results excluded

| | | | | Klebsiella terrigena | | | |
| | | | | Run Results - CFUs/mL by contact time (min) | | | |
| Run Date | # Of Inocula-tions | MPT Run # | Sample # | Challenge Dose | T30 | T60 | T90 |
| --- | --- | --- | --- | --- | --- | --- | --- |
| 30-Apr-03 | 1 | 15 | 4 | 8,700,000 | 2,400 | 0 | 0 |
| | | | 5 | | 2,300 | 0 | 0 |
| 2-May-03 | 2 | 16 | 4 | 5,000,000 | 99 | 0 | 0 |
| | | | 5 | | 5,300 | 0 | 0 |
| 6-May-03 | 3 | 17 | 6 | 4,800,000 | 16,000 | 0 | 0 |
| | | | 7 | | 5,200 | 0 | 0 |
| 20-May-03 | 4 | 20 | 6 | 6,900,000 | 50 | 0 | 0 |
| | | | 7 | | 100 | 18 | 0 |
| 29-May-03 | 5 | 21 | 6 | 4,500,000 | 140,000 | 2 | 0 |
| | | | 7 | | 100 | 3 | 0 |
| 17-Jun-03 | 6 | 22 | 6 | 11,000,000 | 42,000 | 0 | 1 |
| | | | 7 | | 140,000 | 1 | 0 |
| 15-Jul-03 | 7 | 24 | 6 | 10,000,000 | 700,000 | 100 | 0 |
| | | | 7 | | 460,000 | 82 | 0 |
| 7-Aug-03 | 8 | 29 | 6 | 12,000,000 | 430,000 | 1,500 | 3 |
| | | | 7 | | 480,000 | 2,400 | 1 |
| 25-Aug-03 | 9 | 32 | 5 | 8,000,000 | 76,000 | 68,000 | 2,000 |  53
| | | | 6 | | - | 160,000 | 620 |  1

Results in Log Format
No results excluded

| | | | | Klebsiella terrigena | | | |
| | | | | Run Results - CFUs/mL by contact time (min) | | | |
| Run Date | # Of Inocula-tions | MPT Run # | Sample # | Challenge Dose | T30 | T60 | T90 |
| --- | --- | --- | --- | --- | --- | --- | --- |
| 30-Apr-03 | 1 | 15 | 4 | 6.94 | 3.38 | 0.0 | 0.0 |
| | | | 5 | 6.94 | 3.36 | 0.0 | 0.0 |
| 2-May-03 | 2 | 16 | 4 | 6.70 | 2.00 | 0.0 | 0.0 |
| | | | 5 | 6.70 | 3.72 | 0.0 | 0.0 |
| 6-May-03 | 3 | 17 | 6 | 6.68 | 4.20 | 0.0 | 0.0 |
| | | | 7 | 6.68 | 3.72 | 0.0 | 0.0 |
| 20-May-03 | 4 | 20 | 6 | 6.84 | 1.70 | 0.0 | 0.0 |
| | | | 7 | 6.84 | 2.00 | 1.26 | 0.0 |
| 29-May-03 | 5 | 21 | 6 | 6.65 | 5.15 | 0.30 | 0.0 |
| | | | 7 | 6.65 | 2.00 | 0.48 | 0.00 |
| 17-Jun-03 | 6 | 22 | 6 | 7.04 | 4.62 | 0.0 | 0.00 |
| | | | 7 | 7.04 | 5.15 | 0.00 | 0.0 |
| 15-Jul-03 | 7 | 24 | 6 | 7.00 | 5.85 | 2.00 | 0.0 |
| | | | 7 | 7.00 | 5.66 | 1.91 | 0.0 |
| 7-Aug-03 | 8 | 29 | 6 | 7.08 | 5.63 | 3.18 | 0.48 |
| | | | 7 | 7.08 | 5.68 | 3.38 | 0.00 |
| 25-Aug-03 | 9 | 32 | 5 | 6.90 | 4.88 | 4.83 | 3.30 | 1.72
| | | | 6 | 6.90 | - | 5.20 | 2.79 | 0.00

Figure 8A (continued)

Log Reductions
Excluded May 20, T60 result - apparent plate contamination on Sample #7

| | | | | Klebsiella terrigena | | | | |
|---|---|---|---|---|---|---|---|---|
| | | | | Log Reductions by Contact Time (minutes) | | | | |
| Run Date | # Of Inocula-tions | MPT Run # | Sample # | Challenge Dose | T30 | T60 | T90 | T120 |
| 30-Apr-03 | 1 | 15 | 4 | 6.94 | 3.56 | 6.94 | 6.94 | |
| | | | 5 | 6.94 | 3.58 | 6.94 | 6.94 | |
| 2-May-03 | 2 | 16 | 4 | 6.70 | 4.70 | 6.70 | 6.70 | |
| | | | 5 | 6.70 | 2.98 | 6.70 | 6.70 | |
| 6-May-03 | 3 | 17 | 6 | 6.68 | 2.48 | 6.68 | 6.68 | |
| | | | 7 | 6.68 | 2.96 | 6.68 | 6.68 | |
| 20-May-03 | 4 | 20 | 6 | 6.84 | 5.14 | 6.84 | 6.84 | |
| | | | 7 | 6.84 | 4.84 | | 6.84 | |
| 29-May-03 | 5 | 21 | 6 | 6.65 | 1.50 | 6.35 | 6.65 | |
| | | | 7 | 6.65 | 4.65 | 6.17 | 6.65 | |
| 17-Jun-03 | 6 | 22 | 6 | 7.04 | 2.42 | 7.04 | 7.04 | |
| | | | 7 | 7.04 | 1.89 | 7.04 | 7.04 | |
| 15-Jul-03 | 7 | 24 | 6 | 7.00 | 1.15 | 5.00 | 7.00 | |
| | | | 7 | 7.00 | 1.34 | 5.09 | 7.00 | |
| 7-Aug-03 | 8 | 29 | 6 | 7.08 | 1.45 | 3.90 | 6.60 | |
| | | | 7 | 7.08 | 1.40 | 3.70 | 7.08 | |
| 25-Aug-03 | 9 | 32 | 5 | 6.90 | 2.02 | 2.07 | 3.60 | 5.18 |
| | | | 6 | 6.90 | | 1.70 | 4.11 | 6.90 |

Figure 8B

Graph values
May 20 sample #7 result excluded

|  | 30 min | 60 min | 90 min | challenge level |
|---|---|---|---|---|
| 30-Apr-03 | 3.56 | 6.94 | 6.94 | 6.94 |
|  | 3.58 | 6.94 | 6.94 | 6.94 |
| 2-May-03 | 4.70 | 6.70 | 6.70 | 6.70 |
|  | 2.98 | 6.70 | 6.70 | 6.70 |
| 6-May-03 | 2.48 | 6.68 | 6.68 | 6.68 |
|  | 2.96 | 6.68 | 6.68 | 6.68 |
| 20-May-03 | 5.14 | 6.84 | 6.84 | 6.84 |
|  | 4.84 |  | 6.84 | 6.84 |
| 29-May-03 | 1.50 | 6.35 | 6.65 | 6.65 |
|  | 4.65 | 6.17 | 6.65 | 6.65 |
| 17-Jun-03 | 2.42 | 7.04 | 7.04 | 7.04 |
|  | 1.89 | 7.04 | 7.04 | 7.04 |
| 15-Jul-03 | 1.15 | 5.00 | 7.00 | 7.00 |
|  | 1.34 | 5.09 | 7.00 | 7.00 |
| 7-Aug-03 | 1.45 | 3.90 | 6.60 | 7.08 |
|  | 1.40 | 3.70 | 7.08 | 7.08 |
| 25-Aug-03 | 2.02 | 2.07 | 3.60 | 6.90 |
|  |  | 1.70 | 4.11 | 6.90 |
|  |  |  |  |  |

Figure 8C

Average values - 1 per date - for graphing Chart 1

| | 30 min | 60 min | 90 min | challenge level | # of Kleb Challenges |
|---|---|---|---|---|---|
| 30-Apr-03 | 3.57 | 6.94 | 6.94 | 6.94 | 1 |
| 2-May-03 | 3.84 | 6.70 | 6.70 | 6.70 | 2 |
| 6-May-03 | 2.72 | 6.68 | 6.68 | 6.68 | 3 |
| 20-May-03 | 4.99 | 6.84 | 6.84 | 6.84 | 4 |
| 29-May-03 | 3.08 | 6.26 | 6.65 | 6.65 | 5 |
| 17-Jun-03 | 2.16 | 7.04 | 7.04 | 7.04 | 6 |
| 15-Jul-03 | 1.25 | 5.05 | 7.00 | 7.00 | 7 |
| 7-Aug-03 | 1.43 | 3.80 | 6.84 | 7.08 | 8 |
| 25-Aug-03 | 2.02 | 1.88 | 3.86 | 6.90 | 9 |

ORGANIC COMPOUND AND METAL ION SYNERGISTIC DISINFECTION AND PURIFICATION SYSTEM AND METHOD OF MANUFACTURE

CROSS-REFERENCE TO RELATED APPLICATIONS

The present application is a continuation of prior U.S. application Ser. No. 11/947,314, filed Nov. 29, 2007 (now allowed), which is a continuation of prior U.S. application Ser. No. 10/679,660, filed Oct. 6, 2003 (now issued as U.S. Pat. No. 7,485,259), which claims the benefit of U.S. Provisional Application No. 60/416,817, filed Oct. 8, 2002, each of which are hereby incorporated by reference in their entirety.

TECHNICAL FIELD OF THE INVENTION

The present invention relates to antimicrobial compositions principally applicable to the disinfection of water, which compositions utilize the synergistic disinfection properties of selected organic compounds in conjunction with selected metal ions. This disinfection invention may be used in a variety of applications including, but not limited to: public water systems (PWSs); bottled water/stored water; residential Point-of-Use/Point-of-Entry (POU/POE) systems, emergency water disinfection for use in disaster relief situations, military use, hikers, campers, backpackers, commercial flow-through and/or batch treatment devices, water coolers/dispensers, food surface disinfection, fruit and vegetable disinfectant rinses, meat, fish and poultry disinfection, juice and beverage disinfection (including cider), commercial/residential ice production, medical and dental devices, spas, pools, industrial process and wastewater systems, and for potable water and recycled water used in ships, planes, recreational vehicles and spacecraft. This disinfection invention also has widespread applicability for disinfection of water for potable use in third-world and developing countries. The present invention, when used at or below governmentally regulated or recommended potable water concentrations of the individual constituents can provide highly effective water disinfection within minutes or hours, leaving effective residual disinfectant concentrations of the disinfection agents. The present invention can also be used at substantially reduced concentrations while still providing effective disinfection of water for situations in which a disinfection process of minutes or hours is not necessary, such as in the case of stored water not intended for immediate consumption. The present invention can also be used at concentrations higher than those regulated or recommended for potable water for applications in which such potable water concentration limits or recommendations are not applicable such as food rinses, industrial processes and recreational waters.

The present invention can function as a stand-alone disinfectant treatment or may be combined with other purification technologies such as carbon block filtration or other microscreening filtration technologies. This additional purification technology can be used to provide particulate, organic/inorganic contaminant and taste/odor removal as well as providing a size exclusion removal process effective on larger microorganisms such as *Cryptosporidium* and *Giardia*. The present invention may be incorporated with other disinfection technologies such as ultraviolet light, oxidizing chemicals and thermal processes to inactivate or kill organisms such as *Cryptosporidium* and *Giardia*.

The present invention utilizes selected metal ions in combination with natural plant extracts and/or alcohols as the disinfectant.

BACKGROUND ART

Microbiologically safe drinking water is recognized as an essential need by federal and state regulatory agencies, world public health organizations and the lay public. The benefit, to developed (industrialized) and developing nations alike, of a more effective, affordable, broadly applicable and easily applied water treatment disinfection technology cannot be overemphasized.

The World Health Organization (WHO) estimates that approximately 20% of the world's population, or 1.7 billion people, lack access to improved and safe water supplies and that three to four million people, mostly children, die annually from illnesses associated with unsafe drinking water. In the United States, the U.S. Centers for Disease Control and Prevention (CDC) estimates that, including reported and unreported outbreaks, 940,000 cases of illness and potentially 900 deaths occur annually from waterborne microbial infection. Subsets of the general population, including infants, the elderly, organ transplant patients, cancer therapy patients, AIDS patients and other persons with compromised immune systems are at increased risk of waterborne disease.

The U.S. Environmental Protection Agency (EPA) specifies and regulates drinking water quality in the United States for over 170,000 public water systems (PWSs). Of these, over 160,000 PWSs are classified as "small" or "very small" meaning that they serve between 25 and 3,300 people. The present invention may be used as a disinfectant for PWSs. This is significant as EPA has recognized the many drawbacks to chlorine, the most commonly used disinfectant for PWSs. The EPA has expressed interest in and has funded research regarding innovative alternative water treatment technologies. The most significant drawbacks to the use of chlorine as a disinfectant is the formation of disinfection by-products (DBPs), some of which are toxic and suspected carcinogens. This limits the use of chlorine and/or mandates additional treatment to reduce DBP formation. In addition, chlorine's effectiveness can be limited by the physical and/or chemical characteristics of the water sought to be purified. Such limiting factors of chlorine's purification effectiveness include the water's temperature, pH, presence of organic carbon, dissolved organic and inorganic matter, and turbidity. The use of chlorine as a disinfectant also has aesthetic taste and odor concerns as well as safety issues associated with handling the chlorine.

Many of the alternative technologies currently recognized by the EPA in its Alternative Disinfectants and Oxidants Guidance Manual have limitations for widespread use for drinking water disinfection. In addition, many of the alternatives still result in DBP and/or inorganic byproduct formation. With the exception of chlorine dioxide and monochloramine, none of these alternative disinfectants provide residual disinfection in a distribution system or container and therefore typically require the supplemental use of some form of chlorine.

To be a truly effective and robust disinfectant for potable water and many similar applications, it is necessary for the disinfectant/sanitizer to be effective on both bacteria and viruses.

Alternatives to chlorine, such as ions, permanganate, chloramines and ozone/peroxide typically fail to achieve more than a 2-log inactivation of viruses. In some cases these alternative disinfectants provide no measurable inactivation of viruses, particularly in high turbidity, high organic content waters. The use of iodine is recommended by the CDC only for short-term emergency use and has significant adverse taste and aesthetic drawbacks. In summary, none of the recognized alternative disinfectants consistently achieve more than a 3-log inactivation of both bacteria and viruses while also avoiding DBP formation and providing an effective disinfectant residual that can provide microbiologically safe water during extended periods of water storage and/or after the re-inoculation of microorganisms which typically occurs when the stored water is actually used.

In addition to PWSs, there are numerous additional applications for a new, effective, safe method of water disinfection. These include water dispensers in offices and public buildings where there is concern over the microbiological quality of the water, portable water treatment for outdoor activities such as hiking and camping, use in recreational vehicles, seasonal camps and campgrounds, point of use (POU) devices such as softeners and carbon filters, counter top water treatment devices, fruit and vegetable rinses, meat, fish and poultry rinses, storage and transport ice for commercial fishing operations, military uses such as remote field use and for bulk water storage or treatment at military bases, as well as application to ships, airplanes, and the U.S. National Aeronautics and Space Administration (NASA), etc.

Treatment of non-potable water to make it safe to drink from a microbiological perspective for residential use typically involves treatment technologies such as sub-micron filtration, ultraviolet light, ozone, chlorine, iodine and/or other disinfecting chemicals. Some treatment devices make use of resins or media impregnated with biocidal compounds such as iodine so that certain levels of such biocides are released into the water. While size exclusion and ultraviolet light based systems provide essentially immediate removal or inactivation of certain microbes, they do not provide any residual disinfectant to prevent regrowth of organisms. Ultraviolet light based processes are significantly adversely affected by particulates, high organic content, turbidity and a number of chemical constituents and thus fall short of applicability to a wide range of water types. They also require some type of electrical source whether it is (alternating current) AC or (direct current) DC in nature. Size exclusion based methods are typically ineffective on removing viruses as well as some of the smaller bacteria and are impacted by limitations of throughput due to filter plugging.

The present invention represents a novel disinfection technology that utilizes a combination of metal ions and natural derivatives. It is broadly applicable to both untreated natural and/or treated municipal waters that exhibit a wide range of physical/chemical characteristics. As previously described it also is applicable to a wide range of non-drinking water applications including recreational water treatment (hot tubs, swimming pools, therapy pools), dental unit water line devices, food preparation, water re-use, industrial cooling loops, and cooling towers, etc. It can function as a stand-alone disinfection treatment or can be combined with other water treatment technologies.

While use of metal ions either alone, in combinations with other ions, or in combination with other substances such as free chlorine and hydrogen peroxide, has met with some success in bacterial inactivation in certain water types, no combination reported in the scientific literature has proven consistently effective on inactivation of viruses on a wide range of test waters even after extended contact times incorporating hours or even days. This is particularly true when trying to produce microbiologically safe drinking water based on efficacy goals and standards as established by the EPA's Surface Water Treatment Rule (SWTR) and/or in their Guide Standard and Protocol for Testing Microbiological Water Purifiers and using short contact times. Similarly, despite lay claims to the contrary, after extensive testing, citrus extracts such as the type of plant extract used within the most preferred embodiment of the present invention, when used alone, have shown an inability to achieve effective viral reduction even under clean water test conditions such as treated municipal water or untreated natural waters such as water from rivers, streams, brooks, ponds, lakes, springs or wells without protracted contact times. Laboratory testing has confirmed the inability of ions alone or plant extracts alone or the combination of ions and glycerin to achieve effective viral reduction. This same testing has consistently documented the ability of the present invention to achieve viral inactivation under identical and more rigorous test conditions. Laboratory testing using various waters seeded with bacteria and/or viruses using ions alone, plant extracts alone or a combination of ions and an alcohol (glycerin) yielded the following results:

Copper/Silver Ions Alone—Use of silver ions or specific ratios of combined copper and silver ions (10:1 to 30:1) alone resulted in 5 log and 6 log reductions, respectively, on *Klebsiella* after a 60 minute contact time on the seeded municipal water matrix. Copper ions alone were not as effective and yielded reductions of less than 3 log and 5 log after 60 and 240 minutes of contact time, respectively, on seeded municipal water. Copper/silver ion treatment was less effective on *Pseudomonas aeruginosa* in seeded municipal water than on *Klebsiella* with a maximum reduction of less than 5 log being achieved after a 90-minute contact time.

Use of silver or copper ions alone on untreated natural waters such as water from rivers, streams, brooks, ponds, lakes, springs or wells water seeded with *Klebsiella* resulted in log reductions of less than 3-log after 120 minutes of contact time. Use of combined silver and copper ions resulted in log reductions of less than 4-log after 120 minutes of contact time.

No combination of copper/silver ions alone proved even marginally effective on MS2 virus insofar as testing was directed at observing log reductions with minimal contact times, e.g. well less than 24 hours. No reduction in MS2 virus was observed after a contact time of 6 hours and less than 3-log of virus reduction was seen at 24 hours. Similar or even significantly lower inactivation results were achieved on seeded untreated natural waters such as water from rivers, streams, brooks, ponds, lakes, springs or wells with less than 1 log inactivation resulting from the use of copper or copper/silver ions after 4 hours of contact time. No effective reduction of MS2 was achieved using silver ions alone even after contact times of up to 24 hours on seeded municipal water or untreated natural waters such as water from rivers, streams, brooks, ponds, lakes, springs or wells. Therefore, use of copper and/or silver ions alone was judged to be unsatisfactory for disinfection of viruses.

In summary, ions alone, whether used individually or in combination, do not provide acceptable disinfection of municipal or untreated natural waters such as water from rivers, streams, brooks, ponds, lakes, springs or wells for both bacteria and viruses.

Plant Extract i.e. Citricidal™ Alone—The use of Citricidal™ alone, whether dissolved in a water or glycerin base, yielded inconsistent performances on waters seeded with *Klebsiella*. Log reductions on seeded municipal water ranged from 4 log to 6 log after 60 minutes. Log reductions of less than 3 log were seen on seeded untreated natural waters such as water from rivers, streams, brooks, ponds, lakes, springs or wells even after 120 minutes or longer of contact. Citricidal™ was typically completely ineffective on MS2 virus, with no reductions being observed on seeded municipal water or seeded untreated natural waters such as water from rivers, streams, brooks, ponds, lakes, springs or wells even after 24 hours of contact.

In summary, plant extract (i.e. Citricidal™ alone), does not provide acceptable disinfection of municipal or untreated natural waters such as water from rivers, streams, brooks, ponds, lakes, springs or wells for both bacteria and viruses.

Metal Ions and Glycerin (alcohol) Combined—The use of copper and silver ions in conjunction with glycerin yielded inconsistent performances on water seeded with *Klebsiella*. Log reductions on seeded municipal water ranged from 5 log to 6 log after 60 minutes. Log reductions on heterotrophic bacteria on unseeded untreated natural waters such as water from rivers, streams, brooks, ponds, lakes, springs or wells was less than 1.5 log. No reductions of MS2 virus were observed on seeded municipal or untreated natural waters such as water from rivers, streams, brooks, ponds, lakes, springs or wells using a combination of ions and glycerin.

In summary, a combination of ions and glycerin does not provide acceptable disinfection of municipal or untreated natural waters such as water from rivers, streams, brooks, ponds, lakes, springs or wells for both bacteria and viruses.

As previously stated, the present invention represents a unique combination of metal ions together with natural plant extracts and alcohols. As such, it is a new and novel technique and has not previously been reported in the literature or prior art patents. A number of researchers have previously attempted to find suitable alternatives to chlorine disinfection, each of which have well-documented drawbacks. Investigators have tried to take advantage of the antimicrobial properties of copper and silver ions and to optimize their effect, particularly against viruses, by combining them with various other ingredients. However, previous efforts have failed to develop any copper/silver combination disinfectants that have been demonstrated to achieve acceptable inactivation of both bacteria and viruses within short contact times. Some relevant research is briefly reviewed below.

Domek, et al., as disclosed in Domek, M., M. LeChevallier, S. Cameron and G. McFeters, 1984, Evidence for the Role of Copper in the Injury Process of Coliform Bacteria in Drinking Water, Appl. Environ. Microbiol. 48: 289-293, demonstrated that the presence of low levels of copper causes damage to *E. coli* in drinking water samples, and that the effect was dose dependent. Subsequent testing indicated reduced oxygen uptake and glucose utilization by copper-injured cells, as well as changes in metabolic end products.

Kutz, et al., as disclosed in Kutz, S., L. Landeen, M. Yahya and C. Gerba. 1988, Microbiological Evaluation of Copper: Silver Disinfection Units, Proceedings of the Fourth Conference on Progress in Clinical Disinfection, S.U.N.Y., Binghamton, N.Y., Apr. 11-13, 1988, examined electrolytically generated copper (Cu) and silver (Ag) ions alone, free chlorine (FC) alone and Cu/Ag ions plus low levels of FC against seven types of bacteria. Their results indicated that all the bacteria tested were inactivated more rapidly with the combined treatment than by either treatment individually.

Landeen, et al., as disclosed in Landeen, L., M. Yahya, and C. Gerba 1989, Efficacy of Copper/Silver Ions & Reduced Levels of Free Chlorine in Inactivation of *Legionella pneumophila*, Appl. Environ. Microbiol. 55: 3045-3050, also tested copper and silver ions with and without FC, using *Legionella* as the challenge organism, and reported statistically significant improvement in disinfection from the combined treatment.

Yahya, et al., as disclosed in Yahya, M., L. Landeen, M. Mesina, S. Kutz, R. Schultze and C. Gerba, Disinfection of Bacteria in water Systems by Using Electrolytically Generated Copper: Silver & Reduced Levels of Free Chlorine, Can. J. Microbiol. 36: 109-116, conducted similar testing using *Staphylococcus* sp., which previous research had indicated might be more resistant to treatment than coliform bacteria, and reached similar conclusions regarding the benefit of adding FC to the treatment and the limitations of copper/silver ions alone.

Margolin, et al., as disclosed in Margolin, A. B. Control of Microorganisms in Source Water and Drinking Water. pp. 274-284, In: Manual of Environmental Microbiology, Hurst, C. J., Ed., ASM Press, Washington D.C., 2002, evaluated inactivation of MS2 and poliovirus by leached copper with and without added FC. They reported poliovirus showed more resistance to disinfection by copper than MS2 (1.3 log and 4.0 log inactivation in 12 hours, respectively) and that the addition of FC significantly enhanced the inactivation of both viral types.

Abad, et al., as disclosed in Abad, F., R. Pinto, J. Diez and A. Bosch, 1994, Disinfection of Human Enteric Viruses in Water by Copped Silver in Combination with Low Levels of Chlorine, Appl. Environ. Microbiol. 60(7):2377-2383, tested the efficacy of copper and silver ions in combination with low levels of FC against enteric viruses. They reported that copper plus silver plus 0.5 mg/L FC was no more effective against poliovirus than 1 mg/L FC alone. The authors also observed that under the test conditions, adenovirus required 120 minutes of disinfectant contact to achieve 3 log reduction, and Hepatitis A Virus (HAV) and human rotavirus were even more resistant. The authors concluded that (as applied) copper and silver in water may not provide a reliable alternative to high levels of FC for disinfection of viral pathogens. However, they also reported the stability of copper and silver levels in the test chambers, with 75% and 44% of the initial inputs, respectively, detectable after 60 days.

Lin, et. al., as disclosed in Lin, Y., R. Vidic, J. Stout and V. Lu, 1996, Individual and Combined Effects of Copper and Silver Ions on Inactivation of *Legionella Pneumophila*, Wat. Res. 30(8): 1905-1913, examined the efficacy of copper and silver ions, alone and in combination, against *L. pneumophila* serogroup 1. These authors noted that copper was more effective than silver alone, but required a contact time of 2.5 hours to achieve complete (6 log) inactivation of *Legionella* (silver required 24 hours).

Significantly, Lin, et al. also noted that copper and silver ions could result in either additive or synergistic effect, depending upon the concentrations used, and concluded that their combined effect is greater than that observed from either copper or silver alone.

Rohr, et al., as disclosed in Rohr, U., S. Weber, F. Selenka and M. Wilhelm, 2000, Impact of Silver and Copper on the Survival of *Amoebae* and Ciliated Protozoa in Vitro, Int. J. Hyg. Environ. Health 203: 87-89, examined the effect of copper and silver ions against *amoebae* and ciliated protozoa in vitro. The authors reported that within the German drinking water regulatory limits (10 and 100 mg/L for Ag and Cu, respectively), the combined treatment did not inactivate the test protozoa.

Batterman, et al., as disclosed in Batterman, S., K. Mancy, S. Wang, L. Zhang, J. Warila, O., Lev, H. Shuval and B. Fattal, 2001, Evaluation of the Efficacy of a New Secondary Disinfectant Formulation Using Hydrogen Peroxide and Silver and the Formulation of Disinfection By-products Resulting From Interactions With Convention Disinfectants, EPA STAR Grant No. R825362, working under an EPA STAR grant, evaluated the efficacy of combined treatment of hydrogen peroxide ($H_2O_2$) plus copper and silver ions. For bacteria, they reported that the hydrogen peroxide was less effective than silver ions, which was less effective than the combination of $H_2O_2$ and silver ions, which was less effective than $H_2O_2$ plus copper ions. However, the authors concluded that the combined disinfectant achieved unacceptable viral inactivation. Six (6) hours of contact time was required to inactivate 4 logs of MS2 coliphage and the efficacy against poliovirus was even worse, achieving only 0.15 log inactivation after 12 hours of contact time.

As can be seen from the above cited research, while the use of copper and silver ions, either alone or in combination with other substances, has met with success on bacterial inactivation, no combination has proven effective within short contact times on viruses on a wide range of test waters.

Similarly the prior art patents disclose a number of examples of antimicrobial agents that have incorporated metal ions either alone or with other substances. The prior art patents, however, typically teach disinfection systems for non-potable water uses such as swimming pools and spas. In a few instances the prior art patents include treatment systems intended for potable water. None of these prior art patents teach the use of combining EPA potable concentrations of plant extracts, alcohols and metal ions for the disinfection of water of bacteria, algae, protozoans, virus and fingi in water that has an effective kill rate that renders a previously contaminated water source potable in a matter of minutes or hours and that provides disinfectant residual that remains effective for killing or inactivating bacteria and viruses for months or years while not forming disinfection byproducts.

BRIEF DESCRIPTION OF THE DRAWINGS

FIGS. 5 and 6A-6C show the results of a residual efficacy study of a disinfection and purification system according to an embodiment of the present invention; and FIGS. 7 and 8A-8C show the results of a repetitive challenge study of a disinfection and purification system according to an embodiment of the present invention.

DISCLOSURE OF THE INVENTION

Figure 1:
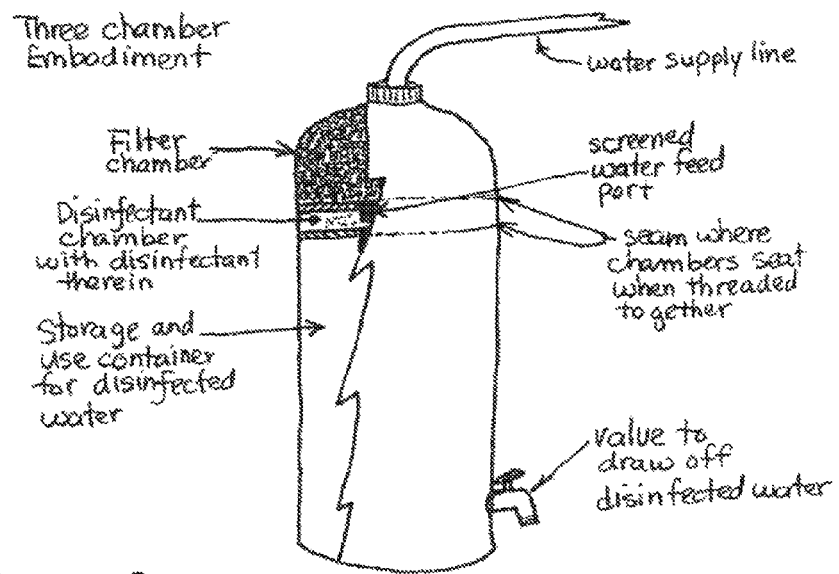
FIGS. 1 and 2 illustrate devices according to embodiments of the present invention.

In view of the foregoing limitations inherent in the known types of disinfection and purification systems which prior art does not anticipate or teach organic compounds in synergistic action with selected metal ions, the present invention provides a disinfection and purification system comprised of organic compounds in synergistic action with selected metal ions and method of manufacture and use that has been designed to allow the user to quickly and effectively disinfect a surface, medium, or fluid such as water of microorganisms such as bacteria, viruses, protozoans, algae and fungi which are improvements that are patently distinct over similar disinfection systems which may already be patented or commercially available. As such, the general purpose of the present invention, which will be described subsequently in greater detail, is to provide a new, novel and useful disinfection and purification system comprised of organic compounds in synergistic action with selected metal ions and method of manufacture and use. There are many additional novel features of this invention directed to solving problems not addressed in the prior art as follows:

the mixture of active ingredients results in a synergistically increased antimicrobial action on user specified surfaces and in user specified mediums or fluids such as water; and a stand-alone treatment technology that may be used to provide disinfection of water such that the resultant water is safe to drink from a bacteriological, virucidal, fungal, algal and protozoan standpoint.

The composition of the treatment mixture in the most preferred embodiment is generally comprised of:

1. A mixture of active ingredients including:
    a) one or more water soluble metal compounds (including, but not limited to metal sulfates, metal salts or metal citrates or some other source of metal ions in solution) to serve as a source in solution of one or more metal ions from the metals in the Periodic Table of the Elements, groups 1b, 2b, 3b, 4b, 5b, 6b, 7b, 8, 3a, 4a, and 5a;
    b) one or more plant extracts; and
    c) one or more alcohols.

The composition of the treatment mixture may also be comprised of:

2. A mixture of active ingredients including:
    a) one or more water soluble metal compounds (including, but not limited to metal sulfates, metal salts or metal citrates or some other source of metal ions in solution) to serve as a source in solution of one or more metal ions from the metals in the Periodic Table of the Elements, groups 1b, 2b, 3b, 4b, 5b, 6b, 7b, 8, 3a, 4a, and 5a; and
    b) one or more plant extracts.

In yet another composition of the treatment mixture it may also be comprised of:

3. A mixture of active ingredients including:
    a) one or more water soluble metal compounds (including, but not limited to metal sulfates, metal salts or metal citrates or some other source of metal ions in solution) to serve as a source in solution of one or more metal ions from the metals in the Periodic Table of the Elements, groups 1b, 2b, 3b, 4b, 5b, 6b, 7b, 8, 3a, 4a, and 5a; and
    b) one or more alcohols.

While generally the main object of this invention is to eliminate the use of disinfecting agents such as chlorine, radiation, ozone/peroxide, and temperature, etc. the following composition of the treatment mixture includes these disinfecting agents, but in significantly reduced concentrations and/or exposures thereby reducing the negative effects of their use:

4. A mixture of active ingredients including:
    a) one or more water soluble metal compounds (including, but not limited to metal sulfates, metal salts or metal citrates or some other source of metal ions in solution) to serve as a source in solution of one or more metal ions from the metals in the Periodic Table of the Elements, groups 1b, 2b, 3b, 4b, 5b, 6b, 7b, 8, 3a, 4a, and 5a; and
    b) one or more plant extracts; and/or
    c) one or more alcohols; and/or
    d) one or more disinfecting compounds such as ozone/peroxide or halogens from the Periodic Table of the Elements, group 7a or derivatives therefrom such as halogenated hydrocarbons, amides, amines, or halogenated dioxides; and/or
    e) exposing the mixture, once it is applied to or mixed with the substance being disinfected, to anti-microbial physical challenges or treatments such as radiation including ultraviolet and infrared, etc., sonic blasts, and temperature extremes, either cold or hot.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims that will be made once the full application is filed.

In this respect, before explaining at least one embodiment of the invention in detail, it is to be understood that the invention, method and apparatus, is not limited in its application to the details of construction and to the arrangements of the components set forth in the following description. The invention, method and apparatus, is capable of other embodiments and of being practiced and carried out in various ways. Also, it is to be understood that the phraseology and terminology employed herein are for the purpose of description and should not be regarded as limiting in any way the scope of this invention or claims made herein.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions and methods insofar as they do not depart from the spirit and scope of the present invention.

Further, the purpose of the foregoing abstract is to enable the U.S. Patent and Trademark Office and the public generally, and especially the scientists, engineers, and practitioners in the art who are not familiar with patent or legal terms or phraseology, to determine quickly from a cursory inspection, the nature and essence of the technical disclosure of the application. The abstract is neither intended to define the invention of the application, which is measured by the claims, nor is it intended to be limiting as to the scope of the invention in any way.

It is therefore an object of the present invention to provide a new, novel and useful disinfection and purification system comprised of organic compounds in synergistic action with selected metal ions and method of manufacture and use which has many of the advantages of the disinfection and purification systems mentioned heretofore and many novel features that result in a disinfection and purification system comprised of organic compounds in synergistic action with selected metal ions and method of manufacture and use which is not anticipated, rendered obvious, suggested, or even implied by any of the prior art disinfection and purification systems and methods of manufacture, either alone or in any combination thereof.

It is another object of the present invention to provide a disinfection and purification system comprised of organic compounds in synergistic action with selected metal ions which may be easily and efficiently manufactured, taught, marketed, and used by the end consumer.

It is a further object of the present invention to provide a disinfection and purification system comprised of organic compounds in synergistic action with selected metal ions which is of a durable and reliable construction.

An even further object of the present invention is to provide a disinfection and purification system comprised of organic compounds in synergistic action with selected metal ions which is susceptible of a low cost of manufacture with regard to both materials and labor, and which accordingly is then susceptible of low prices of sale to the consuming public, thereby making such disinfection and purification system comprised of organic compounds in synergistic action with selected metal ions economically available to the buying public.

Figure 5:
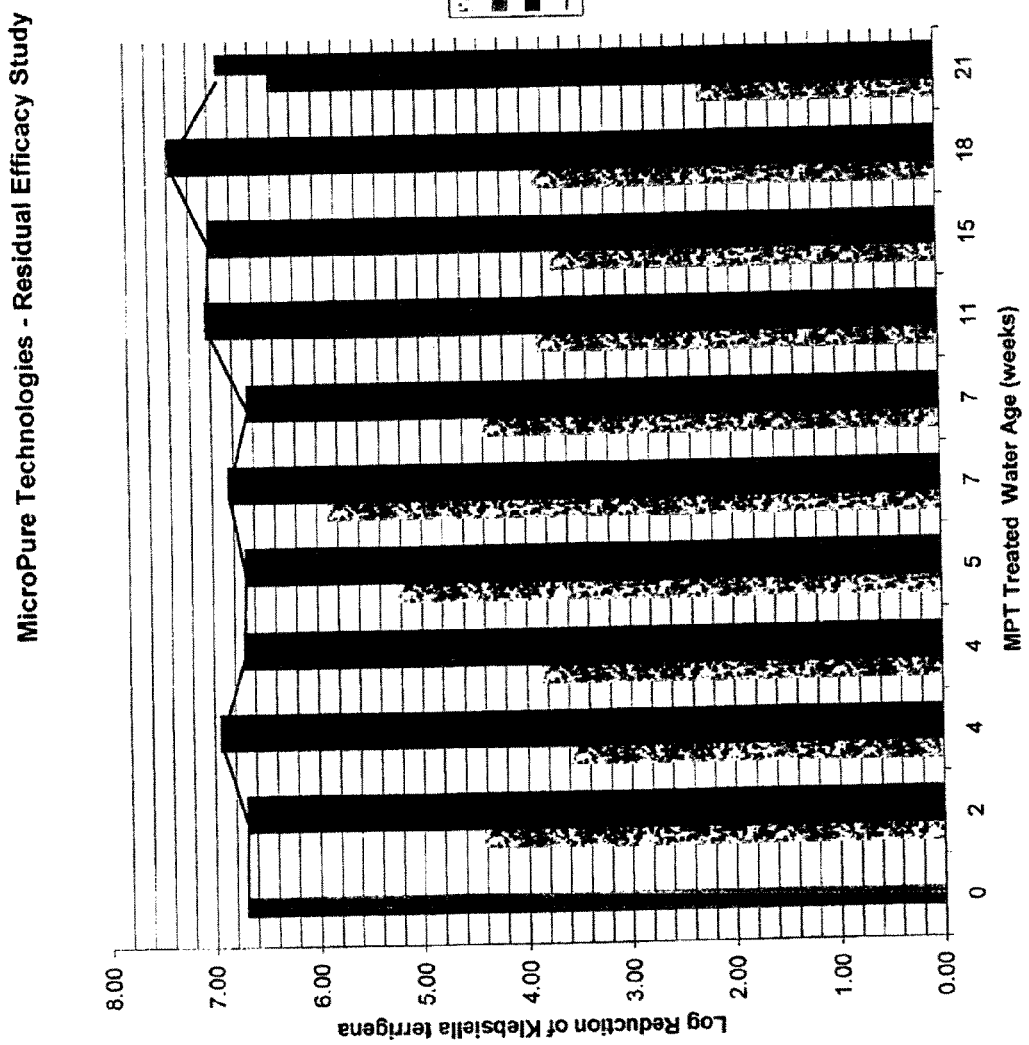

Another object of this invention is to provide a disinfection and purification system comprised of organic compounds in synergistic action with selected metal ions which provides an effective disinfectant residual which persists for months or years. To date, the present invention has been shown to retain its ability to maintain its disinfection and purification action for 21 weeks. A municipal water sample (dechlorinated) was dosed at the most preferred embodiment concentration claimed by the present invention and was stored at ambient conditions. Subsequent to the initial treatment, duplicate aliquots of that treated water were periodically removed and seeded to a concentration of $10^6$ to $10^7$ *Klebsiella* per ml of sample. Log reductions of *Klebsiella* at the 30, 60 and 90 minute contact time remained unchanged throughout the 21 week data collection period with complete inactivation occurring at 60 and/or 90 minutes of contact time. This testing is ongoing and it is expected that the present invention will be able to continue to demonstrate the ability for a stored water sample treated with the present invention to retain its ability to effectively kill bacteria. This ability to effectively maintain a disinfectant residual for extremely long periods of time is a unique feature of the present invention. The results of this Residual Efficacy Study are graphically depicted on FIG. 5 which was prepared from the data presented on FIGS. 6A, 6B and 6C collectively.

Another object of this invention is to provide a disinfection mechanism that allows inactivation of microorganisms in the event that repeated contamination/inoculation of a treated and stored sample of water occurs. In essence, this means that the present invention is not consumed during the first and subsequent disinfection reactions. The ability of the present invention to provide this has been documented through a series of trials. A municipal water sample (dechlorinated) was dosed at the most preferred embodiment concentration claimed by the present invention was stored at ambient conditions. One month after storage an aliquot of the treated water was removed and seeded with $10^6$ to $10^7$ *Klebsiella* per ml of sample. Then, at periodic intervals, that same sample was reinoculated with the same concentration of *Klebsiella* with no further addition of the disinfectant. This occurred over a period of 21 weeks and is still ongoing. Through five inoculations, the inactivation efficacy on *Klebsiella* remained unchanged at 30, 60 and 90-minute contact times with complete kill (6 to 7 log) being observed at 90 minutes. Beginning with the 6$^{th}$ inoculation, a decrease in kill efficacy was observed at the 30 minute contact time. After three additional inoculations, a decrease in the kill efficacy was observed at the 90 minute contact time although, after a contact time of 120 minutes, a complete (7 log) kill of the seeded *Klebsiella* occurred. Ongoing trials will continue this tracking and will include extended contact times beyond 90 minutes to assess the ability of the present invention to provide effective disinfection after additional inoculations. The results of this Repetitive Challenge Study are graphically depicted on FIG. 7 which was prepared from the data presented on FIGS. 8A, 8B and 8C collectively.

Another object of the present invention is to provide a disinfectant solution or material that which, in its finished, combined form, exhibits a long shelf life and that need no special storage conditions. Laboratory testing has documented this to be the case for the present invention. A working solution of the most preferred embodiment concentration of the four components of the present invention was made up and then stored indoors in a sealed container in an uncontrolled temperature environment in South Hero, Vt. for a period of 13 months. This preparation was subjected to extremes in temperature ranging from −20° F. to 100+° F. and was frozen and thawed numerous times during the storage period. It was stored in a translucent container and subjected to natural patterns of daylight and night darkness. Comparison tests were conducted after 13 months of storage between this "stored" disinfectant and freshly made disinfectant. No significant difference in performance on municipal water seeded with $10^6$ to $10^7$ *Klebsiella* per ml of sample was observed between the freshly prepared and the "stored" disinfectant with complete kill of the seeded organisms occurring within a 60 to 90 minute contact time period.

Still yet another object of the present invention is to provide a disinfection and purification system comprised of organic compounds in synergistic action with selected metal ions which provides in the systems of the prior art some of the advantages thereof, while simultaneously overcoming some of the disadvantages normally associated therewith.

These together with other objects of the invention, along with the various features of novelty which characterize the invention, shall be pointed out with particularity in the claims. For a better understanding of the invention, its operating advantages and the specific objects attained by its uses, reference should be had to the accompanying descriptive matter in which there is explained the preferred embodiments of the invention.

BEST MODE FOR CARRYING OUT THE INVENTION

Most Preferred Embodiment—In the most preferred embodiment the invention is used to treat potable water utilizing the two selected metal ions of copper and silver which are placed in solution in the water being treated from either copper sulfate or copper citrate and silver sulfate or silver citrate. The dissolved metal ions are also combined with the plant extract from grapefruit seed and the alcohol glycerin. In this most preferred embodiment the concentration of the active ingredients in the finished water should be:

a) copper at 750 ppb up to no more than the user selected governmental regulatory allowable concentration in potable water (such as applicable EPA or WHO standards);

b) silver at 37.5 ppb up to no more than the user selected governmental regulatory allowable concentration in potable water (such as applicable EPA or WHO standards);

c) the grapefruit seed extract (i.e. Citricidal™) at up to 80-110 ppm (i.e. 10 drops or 100 mg of Nutribiotic™ Brand Grapefruit Seed Extract) up to no more than the user selected governmental regulatory allowable concentration in potable water (such as applicable EPA or WHO standards) if such is applicable; and d) the glycerin up to 160-220 ppm up to no more than the user selected governmental regulatory allowable concentration in potable water (such as applicable EPA or WHO standards) if such is applicable.

In the treatment of potable water, stock solutions may be prepared so that the amount of stock of copper/silver that is added to 1 liter of water will be 1.5 ml and 0.75 ml, respectively. By adjusting the strength of the stock solution, this would change the volume amount quite easily—so if 5 gallons (20 L+/−) of water were being treated there would not be a need to add 30 mls of copper and 15 mls of silver, rather, significantly smaller volumes could be used for packaging convenience and other related considerations and would still have the disinfection efficacy. The commercially available Grapefruit Seed Extract (GSE) known as Citricidal™ is typically packaged commercially in liquid form at 33% Citricidal and 67% glycerin. This establishes the Citricidal™ and glycerin ratios to those described above. However, use of dry powder forms of Citricidal™ and glycerin may result in different ratios of these two components. In addition, the use of Citricidal™ while commercially convenient is not necessary. The use of other plant extracts, either alone or in combination, may be used with equivalent results in disinfection capacity.

Effective disinfection is exhibited with copper/silver ion ratios ranging from 1:1 to 50:1 respectively. The optimum disinfection capacity appears to be a copper to silver ratio of 20:1. For applications of the present invention where longer contact times may be used, such as in stored water not intended for immediate consumption, both the ratios of the ions as well as the concentrations of any or all of the individual constituents comprising the makeup of the present invention have been documented as being able to be significantly reduced. This ability to decrease concentration when providing increased contact time was found to be generally consistent with what is described by the CT Value (Concentration.times.Time) concept, well established in classic disinfection theory. It would therefore be obvious that where the concentrations of these components do not have to meet a governmental regulatory level, much higher concentrations may be used, thereby increasing their antimicrobial effectiveness or vice versa where longer contact times are available then the concentrations may be much lower and the invention will still be effective in rendering potable water. GSE (using the commercially available Citricidal™/Glycerin mixture) is measured using "drops" due to its high viscosity. Forty (40) drops of Citricidal™/Glycerin measured one milliliter using the dropper incorporated into the commercially available GSE bottle. When ten (10) drops of the Citricidal™/Glycerin mixture is used in 1 liter of water to be treated this concentration corresponds to 0.25 mls of Citricidal™/Glycerin per liter of water. While approximately 0.125 mls of Citricidal™/Glycerin or less effectively disinfects synergistically with the copper and silver ions in one liter of filtered water, approximately 0.25 mls of Citricidal™/Glycerin appear to be needed per liter of turbid waters.

The concentration of the most preferred embodiment when dissolved in water, remains substantially unchanged over time thus giving both an effective "immediate" disinfection as well as providing an effective disinfection residual. This characteristic of the invention is especially useful for maintaining potability of stored water where there is a risk of re-inoculation of undesirable microbial agents.

Initial validation trials have been conducted using the most preferred embodiment, as well as trials involving the individual compounds separately and then in combination to arrive at the most preferred embodiment with the maximum synergistic disinfection capacity. The initial trials were conducted on a variety of test waters including filtered, dechlorinated municipal water, a natural surface water (untreated natural waters such as water from rivers, streams, brooks, ponds, lakes, springs or wells) and synthetic water (EPA Test Water #3—as described in the EPA Guide Standard). Tests were conducted using *Klebsiella terrigena, Pseudomonas aeruginosa* and MS2 bacteriophage seeded to the various water types. Bacteria were generally seeded to an initial 6 to 7 log concentration (colony forming units, CFUs, per ml of sample); viruses were generally seeded to attain 5 log concentration (plaque forming units (PFUs) per ml of sample) in each of the test water matrices.

Combining copper and silver ions with Citricidal™ in a glycerin base resulted in a significant synergistic effect, substantially improving disinfection efficacy compared to any of the components alone or in partial combination. Replicate trial/test runs conducted over a period of two years have consistently demonstrated that high log reductions of both bacteria and viruses are achieved by use of this invention on both seeded municipal and seeded untreated natural waters, such as water from rivers, streams, brooks, ponds, lakes, springs or wells, samples rendering such samples microbiologically potable according to EPA and WHO standards.

The most preferred embodiment has achieved complete inactivation (6+ log) on *Klebsiella* in seeded municipal water within 30 minutes and a 4+ log reduction within 60 minutes on seeded untreated natural waters such as water from rivers, streams, brooks, ponds, lakes, springs or wells with turbidities >30 NTU and total organic carbon (TOC) >100 mg/L. *P. aeruginosa* showed complete kill (6+ log) in 90 minutes of contact time on seeded municipal water.

The synergistic effect of the most preferred embodiment is even more pronounced with respect to viruses. Complete inactivation (5+ log) of MS2 in seeded municipal water has been achieved within 15 to 30 minutes of contact time. In seeded untreated natural waters such as water from rivers, streams, brooks, ponds, lakes, springs or wells with turbidities >10 NTU and TOC >200 mg/L, complete (5+ log) inactivation of MS2 occurred within 30 to 60 minutes. In seeded synthetic water (turbidity >30 NTU, TDS 1500 mg/L and pH 9.0—consistent with EPA Test Water #3 as described in the EPA Guide Standard) MS2 reduction was 4+ log within 60 minutes and complete (5+ log) at 120 minutes.

The test results of the most preferred embodiment depicted in FIGS. 5, 6A, 6B, 6C, 7, 8A, 8B and 8C clearly demonstrate that combining copper and silver ions with grapefruit seed extract (i.e. Citricidal™) and glycerol (glycerin) in the above-disclosed manner provides substantially improved disinfection capability as compared to any of the constituents alone or in partial combinations.

Tandem Filtration Mode for Carrying out the Invention

Figure 2:
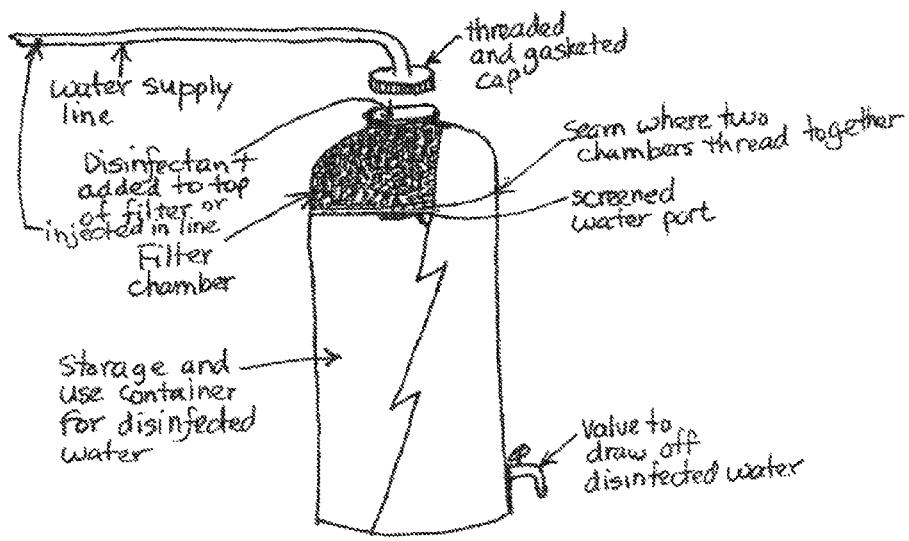

The combined copper and silver ions with Citricidal™ and glycerin disinfectant in the above-disclosed best mode of the invention may also be used in tandem with any combination of filtration means, such as carbon block or micro-pore filters such as those depicted in FIGS. 1 and 2. The combination would allow the filtering out of undesirable particulate or biological matter that may or may not affect the water's potability, but may well negatively impact its aesthetic appeal and potentially its taste.

In the device as depicted in FIG. 1 the water to be disinfected and purified is first run through a standard commercially available carbon block filter at which point the water then passes through a second chamber where the combined best mode disinfectant concentrations of copper and silver ions with Citricidal™ and glycerin have been placed prior, with said disinfectant present in a pre-determined quantity (this may be a tablet, liquid or powdered form) sufficient to disinfect a user selected volume of water. The physical action of the water as it passes through this second chamber forces the combined copper and silver ions with Citricidal™ and glycerin into solution. The water with the dissolved compounds may then pass into a user selected location such as a third chamber or storage container that is sufficient in size to contain the volume of water to be disinfected and purified according to the quantity of disinfectant used.

In yet another embodiment depicted in FIG. 2 the water to be disinfected and purified is first run through a standard commercially available carbon block filter at which point in the same chamber as the carbon block filter the water then passes through combined best mode disinfectant concentrations of copper and silver ions with Citricidal™ and glycerin have been placed prior, with said disinfectant present in a pre-determined quantity (this may be a tablet, liquid or powdered form) sufficient to disinfect a user selected volume of water. Upon leaving the carbon block filter the physical action of the water as it contacts the disinfecting mixture forces the combined copper and silver ions with Citricidal™ and glycerin into solution. The water with the dissolved compounds may then pass into a user selected location such as a second chamber or storage container that is sufficient in size to contain the volume of water to be disinfected and purified according to the quantity of disinfectant used.

Infused Surface Mode for Carrying Out the Invention

Figure 4:
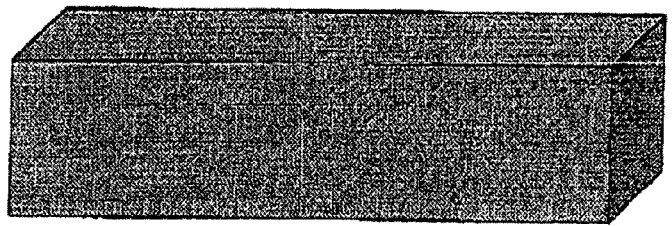

Many industries, such as the food service industry, require the handling of food on surfaces that often support microbial growth that can and does lead to human disease and even death. In the infused surface mode of this invention as depicted in FIG. 4 a suitable semi-permeable material, polymer or similar material is used to manufacture a desired work surface.

Figure 3:
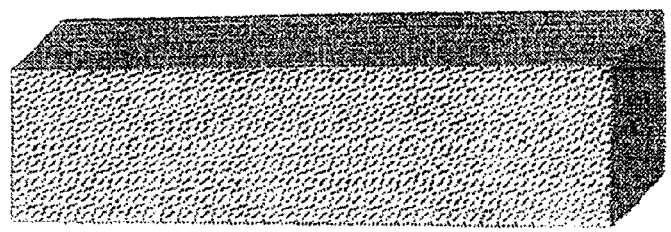
FIGS. 3 and 4 illustrate materials according to embodiments of the present invention.

The material is then treated (treatment can be by injection, immersion, painting, pressure treatment and/or other mechanical means) with the combined copper and silver ions with Citricidal™ and glycerin disinfectant in the above-disclosed best mode of the invention such that the disinfectant is absorbed as completely as possible throughout the material comprising the product. The combined copper and silver ions with Citricidal™ and glycerin disinfectant in the above-disclosed best mode of the invention may also be incorporated in the structure of a material when added as an ingredient in the manufacture of the material, such as composite substances and polymers as depicted in FIG. 3.

During use as a work surface the disinfectant will maintain a disinfecting presence on the surface by leaching, capillary action, mere contact, water activation and/or osmosis/diffusion. This will prevent microbial growth on the surface and thus prevent the spread of contagions and will also deliver disinfectant to substances that may come in contact with the work surface.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships and formulae for the parts of the invention, to include variations in size, quantity of materials, shape, form, function and manner of operation, assembly and use, are deemed readily apparent and obvious to one skilled in the art, and all equivalent relationships to those described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. For example it will be obvious to one skilled in the art to reduce the concentrations and ratios of the active ingredients disclosed in this invention and increase the contact time to achieve a desired disinfection result and vice versa to decrease the contact time needed to achieve a desired disinfection result by increasing the concentrations and ratios of the active ingredients. The novelty of this invention being manifest in the synergistic disinfection effect of the groups of substances or active ingredients disclosed, irrespective of their relative concentrations, recognizing that certain ratios and concentrations of these substances will work better than others as set forth in the most preferred embodiment.

I claim:

1. A disinfection and purification composition comprising:
   (a) copper and silver dissolved in a fluid, wherein a ratio of copper ions to silver ions in the disinfection and purification composition is from 1:1 to 50:1;
   (b) grapefruit seed extract; and
   (c) glycerin,
   wherein the amount of glycerin on a weight basis is less than or equal to 2.75 times the amount of grapefruit seed extract on a weight basis.

2. The composition of claim 1, wherein no more than 110 milligrams of grapefruit seed extract is dissolved in the fluid per liter of the fluid.

3. The composition of claim 1, wherein no more than 220 milligrams of glycerin is dissolved in the fluid per liter of the fluid.

4. The composition of claim 1, wherein a ratio of copper ions to silver ions in the disinfection and purification composition is 20:1.

5. The composition of claim 1, wherein no more than 0.75 milligrams of copper is dissolved in a fluid per liter of the fluid.

6. The composition of claim 1, wherein no more than 0.0375 milligrams of silver is dissolved in a fluid per liter of the fluid.

* * * * *